(12) United States Patent
Shin et al.

(10) Patent No.: US 7,930,886 B2
(45) Date of Patent: Apr. 26, 2011

(54) BIO SIGNAL MEASURING APPARATUS AND METHOD

(75) Inventors: Kun-soo Shin, Seongnam-si (KR);
Jin-sang Hwang, Suwon-si (KR);
Wan-taek Han, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1117 days.

(21) Appl. No.: 11/345,365

(22) Filed: Feb. 2, 2006

(65) Prior Publication Data

US 2006/0173373 A1 Aug. 3, 2006

(30) Foreign Application Priority Data

Feb. 2, 2005 (KR) .................. 10-2005-0009728

(51) Int. Cl.
*A61B 5/04* (2006.01)
(52) U.S. Cl. ........................................................ 60/513
(58) Field of Classification Search .................. 600/391, 600/509, 513, 514, 519, 521, 528
See application file for complete search history.

(56) References Cited

U.S. PATENT DOCUMENTS

| | | | | |
|---|---|---|---|---|
| 3,318,303 A * | 5/1967 | Hammacher | ................. | 600/485 |
| 3,384,981 A * | 5/1968 | Baessler et al. | ............... | 434/266 |
| 3,590,811 A * | 7/1971 | Harris | ............................ | 600/521 |
| 3,841,312 A * | 10/1974 | Corasanti | ....................... | 600/391 |
| 4,220,160 A * | 9/1980 | Kimball et al. | ................ | 600/528 |
| 4,362,164 A * | 12/1982 | Little et al. | ..................... | 600/382 |
| 4,549,552 A * | 10/1985 | Groch et al. | ................... | 128/700 |
| 4,628,939 A * | 12/1986 | Little et al. | ..................... | 600/509 |
| 5,036,857 A | 8/1991 | Semmlow et al. | | |
| 5,178,154 A * | 1/1993 | Ackmann et al. | ............. | 600/526 |
| 5,738,104 A * | 4/1998 | Lo et al. | ......................... | 600/521 |
| 5,807,268 A * | 9/1998 | Reeves et al. | .................. | 600/528 |
| 6,757,392 B1 * | 6/2004 | Granzotto et al. | .............. | 381/67 |
| 7,010,342 B2 * | 3/2006 | Galen et al. | .................... | 600/513 |
| 7,218,966 B2 * | 5/2007 | Haefner | ........................... | 607/17 |
| 2002/0082491 A1 * | 6/2002 | Nissila | ............................ | 600/391 |
| 2003/0176800 A1 * | 9/2003 | Galen et al. | .................... | 600/513 |
| 2004/0215094 A1 * | 10/2004 | Baumer et al. | ................. | 600/528 |

FOREIGN PATENT DOCUMENTS

| | | |
|---|---|---|
| KR | 20-0269580 | 3/2002 |
| KR | 20-0372439 | 12/2004 |

\* cited by examiner

*Primary Examiner* — Mark W Bockelman
*Assistant Examiner* — Roland Dinga
(74) *Attorney, Agent, or Firm* — Sughrue Mion, PLLC

(57) ABSTRACT

A bio signal measuring apparatus. The bio signal measuring apparatus includes an electrocardiogram measuring attached to the skin of a patient to measure an electrocardiogram signal of the patient. A heart sound sensor contacts the skin of the patient to measure a heart sound signal of the patient. A controlling unit obtains bio information including at least a heart rate from the electrocardiogram signal using the heart sound signal.

20 Claims, 6 Drawing Sheets

BIO SIGNAL MEASURING APPARATUS AND METHOD

CROSS-REFERENCE TO RELATED PATENT APPLICATION

This application claims the benefit of Korean Patent Application No. 10-2005-0009728, filed on Feb. 2, 2005, in the Korean Intellectual Property Office, the disclosure of which is incorporated herein in its entirety by reference.

BACKGROUND OF THE INVENTION

1. Field of the Invention

The present invention relates to a bio signal measuring apparatus and method, and more particularly, to an apparatus and method for measuring and analyzing an electrocardiogram and a heart sound.

2. Description of the Related Art

A QRS complex is a signal representing the contraction of a ventricle in an electrocardiogram signal and is required for evaluating a heart state of a user. Particularly, the R peak among QRST peaks composing the QRS complex must be accurately detected.

FIG. 1 shows a typical electrocardiogram signal. Portion "x" indicates the R peak signal and the interval between two R peaks is referred to as an RR interval. The RR interval is the period of time for measuring a heart rate and the R peak is counted during a predetermined period of time to measure the hear rate. Accordingly, the RR interval can be clinically used in arrhythmia diagnosis such as tachycardia, bradycardia, or premature ventricular contraction. Also, the RR interval can provide an index for predicting cardioplegia and an index for evaluating an autonomic nerve function to be applied for the stress evaluation. Also, using the RR interval, an optimal exercise intensity can be provided to the user and an amount of consumed calories can be calculated.

When the user is in a stable state, the R peak can be accurately detected from the electrocardiogram signal. However, when the user is in motion, the R peak can not be accurately detected because the electrocardiogram signal is largely influenced by a noise such as muscle noise, baseline fluctuation due to the breath, or power supply noise, as shown in FIG. 2.

SUMMARY OF THE INVENTION

The present invention provides a bio signal measuring apparatus and method for measuring an electrocardiogram signal and a heart sound and obtaining bio information from the electrocardiogram signal using the measured heart sound signal.

According to an aspect of the present invention, there is provided a bio signal measuring apparatus including an electrocardiogram measuring unit operable to be attached to the skin of a patient to measure an electrocardiogram signal of the patient. A heart sound sensor contacts the skin of the patient to measure a heart sound signal of the patient. A controlling unit obtains bio information including at least a heart rate from the electrocardiogram signal using the heart sound signal.

According to another aspect of the present invention, there is provided a bio signal measuring apparatus including an electrocardiogram measuring unit attached to the skin of a patient to measure an electrocardiogram signal of the patient. A heart sound sensor contacts the skin to measure a heart sound signal of the patient. A controlling unit outputs the electrocardiogram signal and the heart sound signal A portable terminal receives the electrocardiogram signal and the heart sound signal, and obtains bio information from the electrocardiogram signal using the heart sound signal.

According to another aspect of the present invention, there is provided a bio signal measuring method including: measuring an electrocardiogram signal of a patient and detecting an R peak from the electrocardiogram signal using a first threshold value. A heart sound signal of the patient is measured. A window is determined from the heart sound signal. It is determined whether the R peak is detected in the window. Bio information is calculated from a plurality of R peaks which were previously detected if the R peak is detected in the window.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

Figure 1:
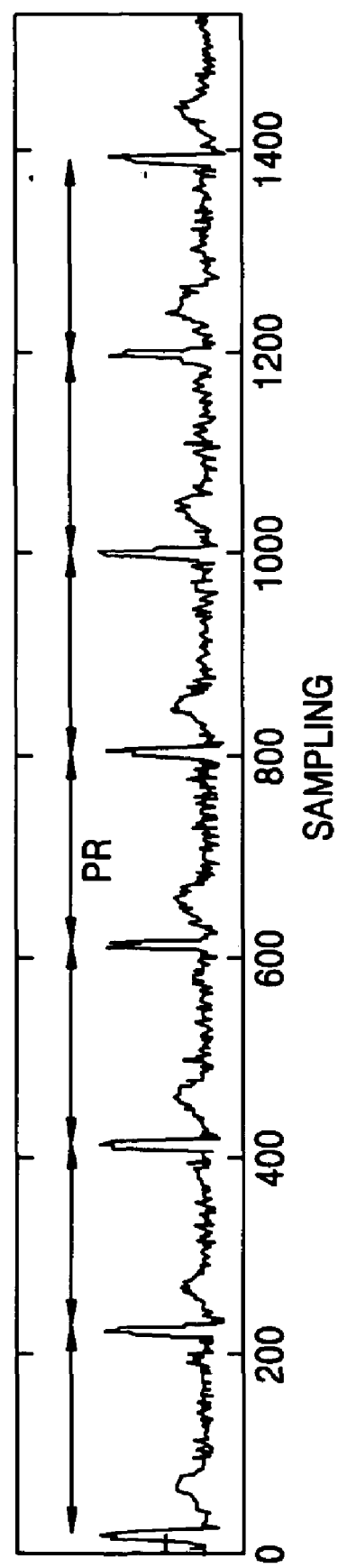
FIG. 1 shows a conventional electrocardiogram signal.
Figure 2:
FIG. 2 shows an example of an electrocardiogram signal which is contaminated by noise.
Figure 3:
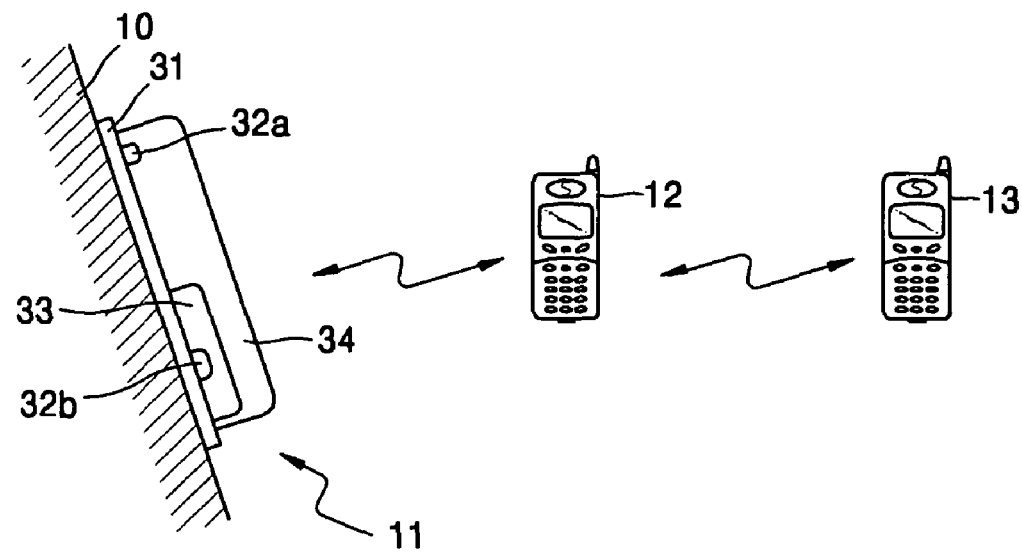
FIG. 3 shows a bio signal measuring apparatus according to the present invention.

FIG. 3 shows a bio signal measuring apparatus according to the present invention. The bio signal measuring apparatus 11 is attached to the skin of a user, measures a bio signal of the user and transmits the bio signal and bio information obtained by processing the bio signal to a portable terminal 12. The bio information may be a heart rate or a heartbeat interval. The portable terminal 12 adequately process the bio signal to obtain the bio information and display the bio information to the user, when receiving the bio signal. In another example, the portable terminal 12 may display the received bio information to the user, when receiving the bio information. The bio signal or the bio information transmitted to the portable terminal 12 is provided to a server (not shown) and further provided to a portable terminal 13 of a specialist such that an advice on the health of the user is received from the specialist.

The portable terminal 12 can carried by the user and communicate with the bio signal measuring apparatus 11 through a local area network such as Bluetooth or a cable via a USB port or a RS232C port. The bio signal measuring apparatus 11 includes a communication means (not shown). Examples of the portable terminal 12 may include a separate device for displaying the bio information, such as a personal digital assistant (PDA), a portable phone, or a notebook computer.

The bio signal measuring apparatus 11 is attached to the skin of the user and measures a potential difference generated during a heart beat when the heart contracts to measure the electrocardiogram signal. The bio signal measuring apparatus 11 includes a body 31, two snaps 32a and 32b, and a controlling unit 34. In the present embodiment, a heart sound sensor 33 is further included in the body 31 in order to measure the heart sound together with the electrocardiogram signal. The heart sound is related to the fremitus generated by the heart contraction when the valve is closing and the blood flows out of the heart.

Figure 4:
FIGS. 4A and 4B show an electrocardiogram signal and a heart sound signal, respectively, measured using the apparatus of FIG. 3.

FIGS. 4A and 4B show an electrocardiogram signal and a heart sound signal, respectively, measured using the apparatus of FIG. 3. The heart sound is divided into a first heart sound signal S1 and a second heart sound signal S2. The first heart sound signal S1 is related to the fremitus generated during the initial period of the ventricular contraction and is the long subenergetic phonation. The second heart sound signal S2 is related to the fremitus generated in the ventricular diastole and is a short shrill. The QRST complex section of the electrocardiogram signal matches the section in which the heart sound signals S1 and S2 are generated. Accordingly, when measuring and comparing the heart sound signal together with the electrocardiogram signal, the R peak is more accurately detected even when the electrocardiogram signal is contaminated by noise.

Figure 5A:
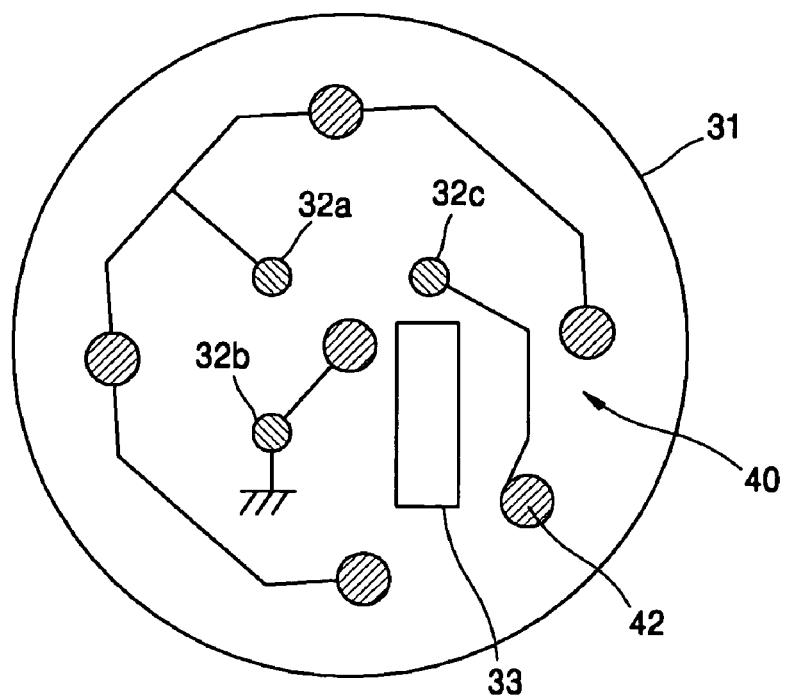
FIG. 5A shows the lower surface of a body of FIG. 3.

FIG. 5A shows the lower surface of the body 31 of FIG. 3. A non-conductive gel 40 is coated on the body 31 to attach the body 31 to the skin of the user. Also, a conductive gel 42 such as Ag or silver chloride is coated on at least three points of the body 31 also to attach the body 31 to the skin and to measure the potential difference of the skin. One point coated with the conductive gel 42 is grounded and the other two points coated with the conductive gels 42 serve for measuring the potential difference. Three points coated with conductive gel 42 are connected with the snaps 32a, 32b, and 32c. The snap 32b is grounded and the other snaps 32a and 32c serve for outputting the potential difference measured via the two non-grounded points to the controlling unit 34. Also, the heart sound sensor 33 which is attached to the skin and measures the heart sound signal is placed on the lower surface of the body 31.

Figure 5B:
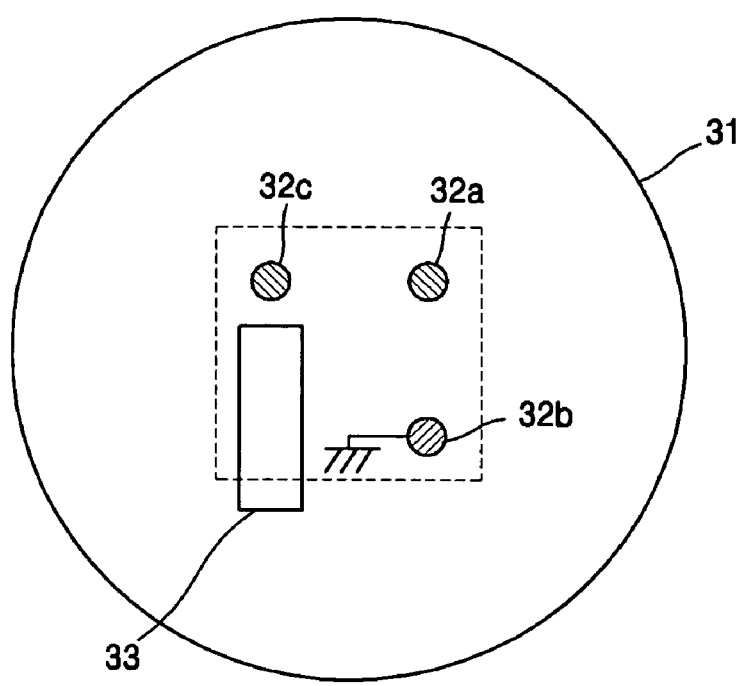
FIG. 5B shows the upper surface of the body of FIG. 3.

FIG. 5B shows the upper surface of the body 31 of FIG. 3. The snaps 32a, 32b, and 32c, the heart sound sensor 33 and the controlling unit 34 are shown in the upper surface of the body 31.

The controlling unit 34 can output the electrocardiogram signal and the heart sound signal output from the snaps 32a, 32b and 32c and the heart sound sensor 33 to the portable terminal 12 or can output the bio information obtained from the electrocardiogram signal and the heart sound signal to the portable terminal 12.

The electrocardiogram signal and the heart sound signal can provide various pieces of health information. For example, an abnormal state such as arrhythmia or myocardial infarction can be identified by obtaining the heart rate or the heartbeat interval from the electrocardiogram signal. Also, it is possible to know whether the value is in an abnormal state by obtaining the interval between the heart sound signals S1 and S2 or the amplitudes of the heart sound signals S1 and S2. That is, the heart sound signals S1 and S2 are sounds made when the valve of the heart closes and an abnormal fremitus which may be made between the heart sound signals S1 and S2 is referred to as a cardiac murmur. Since the cardiac murmur is generally made by the leakage (back flow) or the constriction of the heart valve, it can be determined whether the heart valve is in the abnormal state by the interval between the heart sound signals S1 and S2 or the amplitudes of two heart sound signals S1 and S2.

Accordingly, the electrocardiogram signal and the heart sound signal are received by the portable terminal 12, transmitted to a server (not shown) and further transmitted to a portable terminal of a specialist, such that an advice on the health of the user can be received from the specialist.

Figure 6:
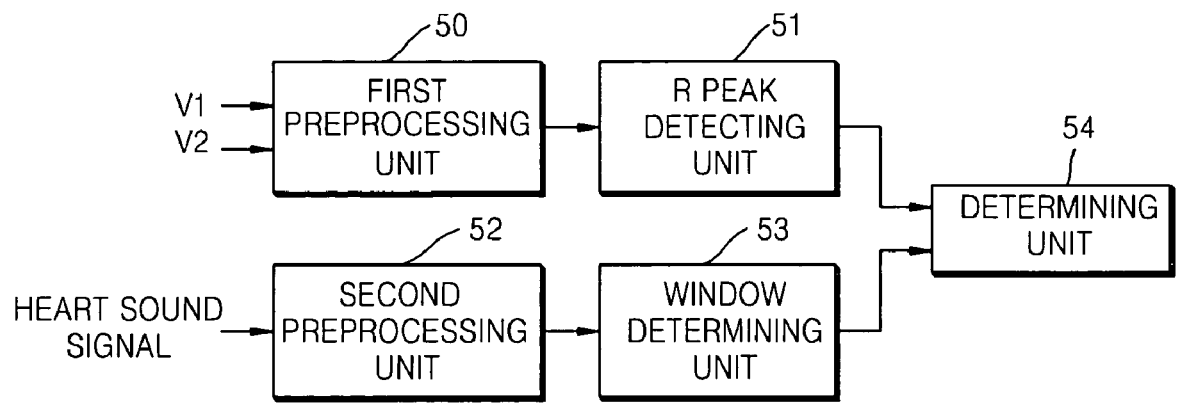
FIG. 6 is a detailed block diagram of a bio signal processing unit included in a portable terminal or a controlling unit.

FIG. 6 is a detailed block diagram of a bio signal processing unit (not shown) included in the portable terminal 12 or the controlling unit 34. The controlling unit 34 or the bio signal processing unit includes a first preprocessing unit 50, an R peak detecting unit 51, a second preprocessing unit 52, a window determining unit 53, and a determining unit 54.

Figure 7:
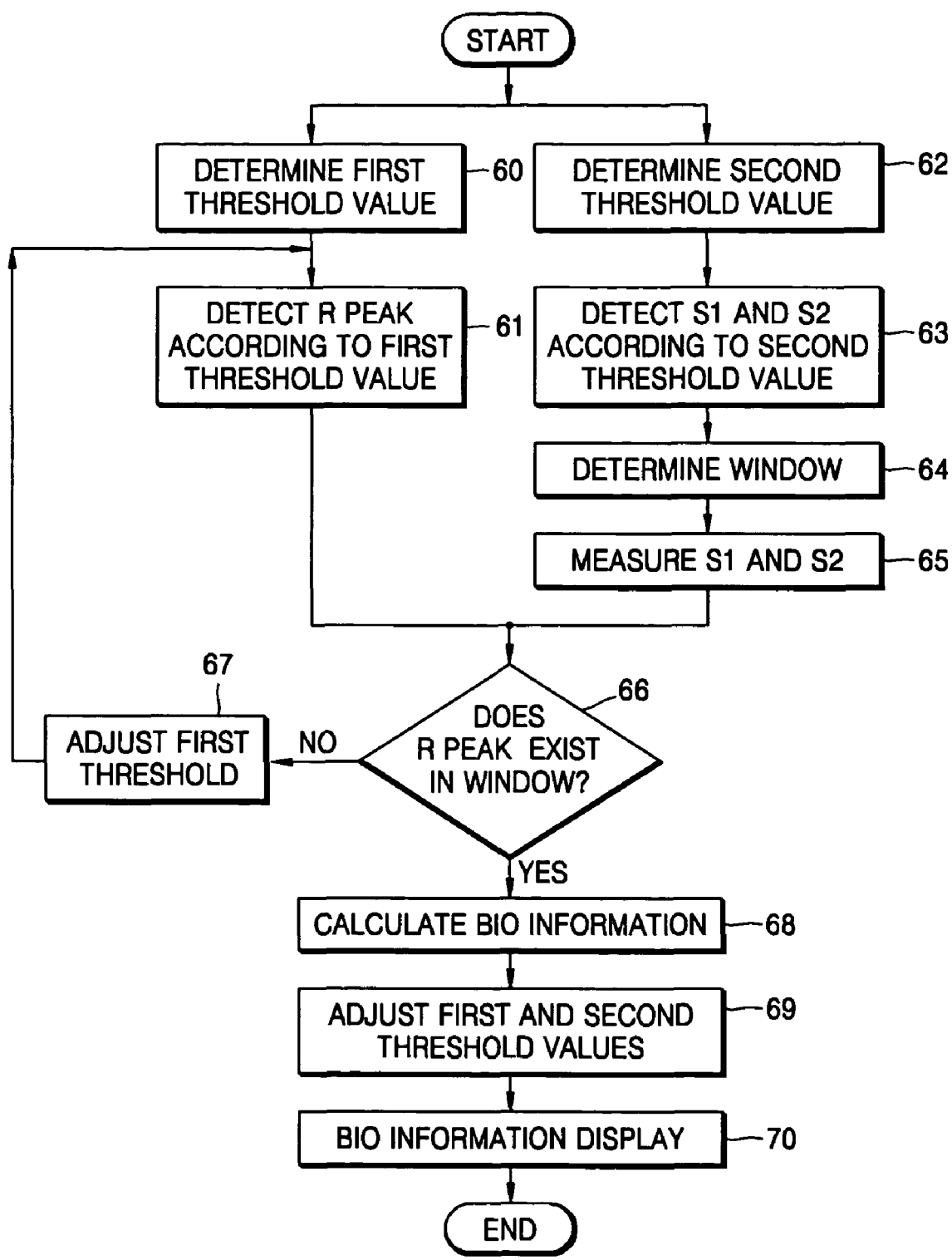
FIG. 7 is a flowchart showing a bio signal measuring method according to the present invention.

The operation of the controlling unit 34 or the bio signal processing unit will be described with reference to FIG. 7.

The first preprocessing unit 50 stores, amplifies, and filters the electrocardiogram signal measured during a predetermined period, for example, 30 seconds. Also, a first threshold value for detecting the R peak is determined from the filtered signal (operation 60). Since the first threshold value may vary according to the electrocardiogram signal of the user, the first preprocessing unit 50 initially uses a previously set value to detect the R peak and then this value is updated to an adequate value by repeated measurements.

The R peak detecting unit 51 detects the R peak from the electrocardiogram signal using the first threshold value to measure the amplitude thereof (operation 61).

The second preprocessing unit 52 stores, amplifies, and filters the heart sound signal measured during a predetermined period, for example, 30 seconds. Also, a second threshold value for detecting the heart sound signals S1 and S2 is determined from the heart sound signal (operation 62). Since the second threshold value may also vary according to the heart sound signal of the user, the second preprocessing unit 52 initially uses a previously set value to detect the heart sound signal and then this value is updated to an adequate value by repeated measurements.

The window determining unit 53 detects the heart sound signals S1 and S2 of the heart sound signal according to the second threshold value (operation 63) and determines a window in which the R peak is detected using the heart sound signals S1 and S2 (operation 64). Here, the width of the window is large enough to enclose the heart sound signals S1 and S2 in consideration of the interval between the detected heart sound signals S1 and S2.

The window determining unit 53 detects an envelope of the heart sound signal and measures the interval between the heart sound signals S1 and S2 and the peak amplitudes of the heart sound signals S1 and S2 from the envelope, after determining the window (operation 65).

Next, it is determined whether the R peak detected in operation 61 exists in the window (operation 66). If the R peak does not exist in the window, the first threshold value is adjusted (operation 67), the R peak is detected from the electrocardiogram signal again, and it is determined whether the detected R peak exists in the window. The adjustment of the first threshold value is accomplished by multiplying the first threshold value by any value which is greater than 0 and is less than 1. That is, the reason that the R peak is not detected in the window is because the first threshold value is greater than the amplitude of the R peak. Accordingly, the first threshold value is adjusted to a smaller value.

If the R peak exists in the window in operation 66, the RR interval is obtained from the plurality of the R peaks which were previously detected to calculate the bio information such as the heart rate (operation 68) and the first and second threshold values are adjusted using the bio information and efficient parameters, that is, the amplitudes of the heart sounds S1 and S2 (operation 69).

The first and second threshold values can be adjusted by Equation 1.

$$TH1 = TH1*\beta + A_R*(1-\beta)$$
$$TH2 = Th2*\gamma + A_{S1,S2}*(1-\gamma) \quad \text{[Equation 1]}$$

Where: TH1 and TH2 are the first threshold value and the second threshold value, respectively; $0 < \beta, \gamma < 1$; $A_R$ is the amplitude of the R peak; $A_{S1, S2}$ is the amplitude of the heart sound signals S1 and S2 or the average thereof.

The first threshold value and the second threshold value are adaptively adjusted when the baseline fluctuation of the electrocardiogram signal or the heart sound signal is changed.

The bio information is displayed to the user through the portable terminal 12 (operation 70).

Aspects of the invention, can also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, optical data storage devices, and carrier waves (such as data transmission through the Internet). The computer readable recording medium can also be distributed over network coupled computer systems so that the computer readable code is stored and executed in a distributed fashion. Also, functional programs, codes, and code segments for accomplishing the present invention can be easily construed by programmers skilled in the art to which the present invention pertains.

According to the present invention, the heart sound signal is detected together with the electrocardiogram signal, the R peak is detected with reference to the heart sound signal, and thus the R peak can be more accurately detected even when the user is in motion.

Also, since the heart rate can be accurately calculated according to the accurate detected R peak, the suitable exercise intensity can be provided to the user when the user works out and arrhythmia can detected from the RR interval. Also, since the heart rate can be measured during a predetermined period, the autonomic nerve function or the stress evaluating function can be obtained through the analysis of the heart rate variation.

Further, it can be determined whether the valve of the heart is in an abnormal state, and the contractility of the cardiac muscle can be evaluated. Also, the preload, which represents the amount of blood filled in the ventricle at the ventricular ejection time or the diastole of the ventricle can be evaluated.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A bio signal measuring apparatus comprising:
   a body operable to be attached to a skin of a patient;
   an electrocardiogram measuring unit disposed on the body and operable to be attached to the skin of the patient to measure an electrocardiogram signal of the patient;
   a heart sound sensor disposed on the body and operable to contact the skin of the patient to measure a heart sound signal of the patient; and
   a controlling unit disposed on the body and operable to obtain bio information including at least a heart rate from the electrocardiogram signal with reference to the heart sound signal, and to detect a window such that the window contains a first heart sound and a second heart sound of the heart sound signal,
   wherein the bio information is obtained based on a result of determining whether an R peak of the electrocardiogram signal exists in the detected window.

2. The apparatus according to claim 1, wherein the electrocardiogram measuring unit comprises:
   conductive gels coated on at least three points on a surface of the body; and
   a plurality of snaps connected to the conductive gels, one of said plurality of snaps being grounded and two of said plurality of snaps output a potential difference therebetween as the electrocardiogram signal.

3. The apparatus according to claim 2, wherein a non-conductive gel is coated on the surface of the body except on the at least three points to make the body adherable to the skin.

4. The apparatus according to claim 1, wherein the controlling unit comprises:
   an R peak detecting unit operable to detect the R peak from the electrocardiogram signal using a first threshold value;
   a window determining unit operable to detect the first heart sound signal and the second heart sound signal from the heart sound signal using a second threshold value and further operable to detect the window such that the window contains the first heart sound and the second heart sound; and
   a determining unit operable to determine whether the R peak exists in the window and further operable to calculate the bio information from a plurality of R peaks.

5. The apparatus according to claim 4, wherein the apparatus is operable to adjust the first threshold value if the determining unit determines that the R peak does not exist in the window, and the R peak detecting unit is operable to detect the R peak from the electrocardiogram signal using the adjusted first threshold value again.

6. The apparatus according to claim 4, wherein the first threshold value and the second threshold value are adjusted by using the amplitude of the first heart sound signal or second heart sound signal and the amplitude of the R peak if the determining unit determines that the R peak exists in the window.

7. The apparatus according to claim 1, further comprising a portable terminal operable to receive the bio information.

8. The apparatus according to claim 7, where the portable terminal is operable to display the bio information.

9. The apparatus according to claim 1, wherein the body with the electrocardiogram measuring unit, the heart sound sensor, and the controlling unit comprise a portable unit, which is operable to be attached to the skin of the patient in motion.

10. The apparatus according to claim 9, wherein the controlling unit obtains the R peak from the electrocardiogram signal based on the obtained heart sound signal while the patient is in motion, calculates the bio information based on the R peak, and provides the bio information for evaluation of the patient in motion.

11. A bio signal measuring apparatus comprising:
    a body operable to attach to a skin of a patient;
    an electrocardiogram measuring unit provided on the body and operable to attach to the skin of the patient to measure an electrocardiogram signal of the patient;
    a heart sound sensor disposed on the body and operable to contact the skin of the patient to measure a heart sound signal of the patient;

a controlling unit disposed on the body and operable to output the electrocardiogram signal and the heart sound signal and to detect a window such that the window contains a first heart sound and a second heart sound of the heart sound signal; and a portable terminal operable to receive the electrocardiogram signal and the heart sound signal, and further operable to obtain bio information including at least a heart rate from the electrocardiogram signal with reference to the heart sound signal, wherein the bio information is obtained based on a result of determining whether an R peak of the electrocardiogram signal exists in the detected window.

12. The apparatus according to claim 11, wherein the electrocardiogram measuring unit comprises:

conductive gels coated on at least three points of a surface of the body; and a plurality of snaps operable to be connected to the conductive gels, one of said plurality of snaps being grounded and two of said plurality of snaps operable to output a potential difference therebetween as the electrocardiogram signal.

13. The apparatus according to claim 12, wherein a non-conductive gel is coated on the surface of the body except on the at least three points to make the body adherable to the skin.

14. The apparatus according to claim 11, wherein the controlling unit comprises:

an R peak detecting unit operable to detect the R peak from the electrocardiogram signal using a first threshold value;

a window determining unit operable to detect the first heart sound signal and the second heart sound signal from the heart sound signal using a second threshold value and further operable to determine the window such that the window contains the first heart sound and the second heart sound; and a determining unit operable to determine whether the R peak exists in the window and further operable to calculate the bio information from a plurality of R peaks.

15. The apparatus according to claim 14, wherein the apparatus is operable to adjust first threshold value if the determining unit determines that the R peak does not exist in the window, and the R peak detecting unit is operable to the R peak from the electrocardiogram signal using the adjusted first threshold value again.

16. The apparatus according to claim 14, wherein the first threshold value and the second threshold value are adjusted by using the amplitude of the first or second heart sound signal and the amplitude of the R peak if the determining unit determines that the R peak exists in the window.

17. A bio signal measuring for a bio signal measuring apparatus comprising:

a body operable to be attached to a skin of a patient;

an electrocardiogram measuring unit disposed on the body and operable to be attached to the skin of the patient to measure an electrocardiogram signal of the patient;

a heart sound sensor disposed on the body and operable to contact the skin of the patient to measure a heart sound signal of the patient; and a controlling unit disposed on the body and operable to obtain bio information including at least a heart rate from the electrocardiogram signal with reference to the heart sound signal and to detect a window such that the window contains a first heart sound and a second heart sound of the heart sound signal, wherein the bio information is obtained based on a result of determining whether an R peak of the electrocardiogram signal exists in the detected window, the method comprising:

measuring the electrocardiogram signal and detecting the R peak from the electrocardiogram signal using a first threshold value;

measuring the heart sound signal and determining the window from the heart sound signal;

determining whether the R peak is detected in the window; and calculating the bio information from a plurality of R peaks which were previously detected if the R peak is detected in the window.

18. The method according to claim 17, wherein during determining the window, the first heart sound signal and the second heart sound signal are obtained from the heart sound signal using a second threshold value and a size of the window is determined such that the window contains the first heart sound signal and the second heart sound signal.

19. The method according to claim 18, wherein the first threshold value is adjusted using the amplitude of the R peak and the second threshold value is adjusted using the amplitude of the first heart sound signal or the second heart sound signal.

20. The method according to claim 17, wherein the first threshold value is adjusted and the R peak is detected using the first threshold value again if the R peak is not detected in the window.

\* \* \* \* \*